(12) United States Patent
Gross

(10) Patent No.: US 6,171,286 B1
(45) Date of Patent: Jan. 9, 2001

(54) SELF-ALIGNING SYRINGE PLUNGER

(76) Inventor: James R. Gross, 125 Shore Dr., Portage, IN (US) 46368

( * ) Notice: Under 35 U.S.C. 154(b), the term of this patent shall be extended for 0 days.

(21) Appl. No.: 09/296,387

(22) Filed: Apr. 20, 1999

(51) Int. Cl.[7] .................................................. A61M 5/315
(52) U.S. Cl. .......................................... 604/228; 604/218
(58) Field of Search .................................... 604/218, 219, 604/222, 227, 228, 229

(56) References Cited

U.S. PATENT DOCUMENTS

| | | | |
|---|---|---|---|
| 2,641,093 | * | 6/1953 | Kolodny et al. ...................... 604/218 |
| 2,832,340 | * | 4/1958 | Dann et al. ........................... 128/218 |

* cited by examiner

Primary Examiner—John G. Weiss
Assistant Examiner—Ann Lam
(74) Attorney, Agent, or Firm—Alvin Isaacs

(57) ABSTRACT

Disclosed is a syringe plunger adapted for use with a glass syringe barrel to provide a low friction syringe useful in medical procedures such as administering epidural anesthesia, the plunger having a first or leading member and a second or trailing member, the first member comprising a hollow glass tubular body defining a chamber having a closed leading end and an open trailing end, the first member being characterized as adapted to provide a very close tolerance fit within the glass syringe barrel and as exhibiting substantially no frictional interference as the leading end of the first member is advanced axially within the syringe barrel; the second member having leading and trailing ends; and means for flexibly securing the leading end of the second member within the chamber of the first member so that the second member is free to flex at the point of attachment in response to lateral forces applied to the second member as the plunger is advanced within the glass barrel, the plunger thereby being characterized as being self-aligning, thereby preventing the lateral forces applied to the plunger from moving the first member out of axial alignment with the axis of the barrel to cause binding or dragging of the plunger within the barrel, this being the stated task of the invention.

18 Claims, 6 Drawing Sheets

SELF-ALIGNING SYRINGE PLUNGER

FIELD OF THE INVENTION

This invention relates to glass syringes which are particularly useful in certain sensitive medical procedures as well as for precise laboratory uses.

Since the invention is directed primarily to improvements in low friction syringes for use in administering epidural anesthesia, the invention will be described in detail hereinafter with reference to this medical procedure.

BACKGROUND OF THE INVENTION

Glass syringes are considered by medical practitioners to be the most sensitive of all the types of syringes currently produced. This extreme sensitivity is a result of the precise tolerances utilized in the manufacturing process. Typically, in these manufacturing procedures, both the exterior surface of the syringe plunger (piston) and the interior surface of the barrel in which it is to be seated for administering fluid are treated to a grinding and/or bead-blasting step which imparts a very fine texture to these mating surfaces. This process when combined with a very close tolerance fit results in a closely matched assembly which does not exhibit the typical drag or frictional interference associated with syringes manufactured from plastic or other non-glass materials as the plunger moves axially towards the distal (leading end) of the barrel.

The matched ground glass syringes provide a smooth, friction-free movement of the syringe plunger within the syringe barrel effective in the movement of either air or liquid through the syringe. Although the plunger and barrel surfaces do not actually touch, assuming the plunger moves forward axially in the barrel, their close proximity entraps air or liquid molecules between their surfaces sufficient to create an air- or liquid-tight interface. This close fit results in an effortless seal between the plunger and barrel. Total expulsion of air or liquid from the syringe is accomplished without any leakage from between the mating surfaces and is further accomplished with a minimal and, in some cases, immeasurable amount of force on the plunger.

Although the attributes of the matched component ground glass syringes are uncontested, they are not without certain limitations or inherent problems.

As was mentioned above, the plunger and barrel surfaces do not actually touch provided that the plunger moves forward axially within the barrel.

However, as will be discussed in detail hereinafter, there is a tendency in the manipulation of the plunger for it to move distally in the barrel in a non-axial manner which, in turn, will cause "sticking" and "freezing up" such that the plunger becomes inoperable for its intended use. This problem is repeatedly described in the medical literature, including, but not limited to training texts for epidural anesthesia, and the patent literature, such as Col. 1, lines 10–29 of Applicant's U.S. Pat. No. 5,397,313 for a LOW FRICTION SYRINGE issued Mar. 14, 1995.

If this problem occurs during the precise procedure described as the "loss of resistance technique" for locating the epidural space, the anesthesiologist will be thwarted in the attempt to locate the epidural space and the patient is put into certain risk in the administration of epidural anesthesia.

The technique for locating the epidural space is well described in the literature (citations not needed) describing the loss of resistance technique. As described and well known by those skilled in the art, a glass syringe is filled with air, liquid or a combination of both and attached to an epidural needle. Once so attached, the needle is advanced through the delicate tissues of the spineous ligaments of the patient. Constant or pulsating pressure is applied to the syringe plunger while the tip of the epidural needle moves forward through the interspineous tissues. A tactile sensation of resistance to the forward movement of the plunger and the spring-like rebound of the plunger when pressure is released indicate to the anesthesiologist that the needle is still within the interspineous ligaments and that the precise location of the epidural space has not been reached.

If the plunger should suddenly stick or freeze up, then the entire procedure is put at risk because the needle cannot, with certainty, be advanced toward the epidural space. Furthermore, location of the epidural space will not be indicated by the free movement of the syringe plunger. When the plunger sticks or freezes up, then the procedure must be abandoned until the syringe is replaced.

It is apparent from the aforementioned description that limitations of a significant nature exist with the current, state of the art, glass syringes. It is further apparent that there exists a need for an improved glass syringe.

Stated simply, the task of the present invention is to provide a glass syringe which does not exhibit the foregoing limitations which may be described as sticking or freezing up.

These limitations occur most frequently when pressure applied to the plunger moves the plunger out of axial alignment with the axis of the syringe barrel. This misalignment of plunger and barrel results in the leading edge and the surface of a trailing portion of the plunger binding or dragging against the ground glass surface of the bore of the syringe barrel. The cushion of air or liquid which imparts the friction-free movement of the plunger through the barrel is eliminated and the ground glass surfaces drag on one another or bind together, resulting in the limitations or deficiencies inherent in the system known in the art as sticking or freezing up.

Due to the low frictional resistance between the glass plunger and glass barrel, a high degree of sensitivity to pressure changes is imparted to the fingers of the anesthesiologist. This sensitivity is of paramount importance to the success of the procedure and, ultimately, to the correct placement of the epidural needle within the epidural space. The sensitivity so described is dependent upon the anesthesiologist's manipulation of the syringe plunger and herein lies the basis and cause of the aforementioned limitations to which the task of this invention is directed to obviating.

It is pointed out that the human hand is not completely capable of holding a syringe barrel between the index and middle fingers and simultaneously to pulsate the syringe plunger without imparting a lateral or non-axial force to the plunger. This mis-aligning motion was readily apparent to Applicant after he studied and analyzed the motion of the thumb in relation to the adjoining index and middle fingers; and Applicant believes it will be equally obvious to those skilled in the art in the light of the foregoing description.

Specifically, the thumb describes an arc as it pivots from the thumb joint in relation to the stationary first and second fingers. This unaligned motion imparts a lateral force to the plunger as it is moved within the barrel.

The following patents have been found as the result of a novelty search of the subject matter of this application. No other prior art relevant to the present invention is known to Applicant or his attorney.

U.S. Pat. No. 782,723 issued to Campbell relates to a hypodermic syringe for antitoxin serum having for its object the provision of an improved piston and operating handle therefor by the use of which it is possible to impart a rotary motion to eject serum from the barrel of the syringe, even though the piston adheres firmly to the walls of the barrel, due to the use of cement or by the gumming action of the serum itself. The patent discloses a glass barrel and a rubber piston which can be actuated with a screwdriver-like projection E (FIG. 4). It appears that the screwdriver-like projection is moveable within a slot $f$ disclosed in FIG. 4. Although it is conceivable that the screwdriver-like projection could be rotated within the slot, such rotation is not disclosed.

U.S. Pat. No. 2,102,591 to Hagemeier relates to a dental syringe of the kind wherein the plunger or piston is operated by a pair of hand grips, the object of the invention being to obtain a syringe of this kind which allows of a gradual, stepwise discharge of its contents in predetermined quantities and in which the plunger is in the form of a screw spindle on which the operating elements act through the medium of an adjustable nut by which the position of the syringe can be regulated. In Col. 2, page 1, in the discussion of using the syringe for filling teeth with cement, it is disclosed that a piston 26 may be employed to which the plunger 17 may be connected by means of a ball joint, the ball 27 being attached or formed with a socket 28 applied to the plunger.

U.S. Pat. No. 2,354,649 to Bruckner also relates to a dental syringe which has a novel form of plunger designed to prevent the disruptive wedging forces occurring with axial misalignment of the plunger and barrel of a syringe. The syringe accommodates insertable glass vials having a rubber plug closure at each end. The discharge end of the syringe is provided with a hollow needle which punctures one of the plugs, while the other end of the syringe is provided with a finger grip and plunger, the plunger being axially slidable and engageable with the other of the plugs, the other plug then acting as a piston to eject fluid from the vial. An object of the invention (col. 1) is stated to be to permit self-adjustment of the plunger head with respect to the vial and piston and thus to eliminate "those side thrusts or strains on the vial walls, due to this wedging action" . Another object is to provide a plunger made in two parts and having a swivel connection between the parts. This is accomplished with a ball and joint linkage. "Since the plunger head is free to swivel slightly relative to the piston, there results a three link kinematic chain, comprising the piston and two parts of the plunger, in contrast with the self jamming of the two link trains of the prior art."

U.S. Pat. No. 2,832,340 issued to Dann et al. relates to a "syringe push rod" attached to a plunger and being especially adapted for use in disposable syringes. When the syringe is filled with fluid, the push rod has a relatively short bearing on the interior surface of the syringe and it is said that the push rod may inadvertently be thrown out of axial alignment by the user. With prior push rods rigidly attached to the plunger, it is said that cocking of the plunger will occur and the cocked plunger will allow a small amount of drug seepage proximally. This problem is said to be obviated by providing a flexible connection between the push rod and the plunger. As disclosed, means are provided at the distal end of the push rod for positive engagement with the syringe plunger providing positive control of aspiration and injection, the means being attached to the push rod by a flexible web or elastic diaphragm, thus permitting a limited degree of axial misalignment of the push rod without a corresponding cocking of the plunger in the syringe barrel. The means for connecting the push rod to the plunger may, for example, be a socket mating with a threaded stud on the plunger, or a stud mating with a threaded metal socket in the plunger, or a threaded stud mating with a threaded recess molded in the plunger material.

U.S. Pat. No. 3,175,646 granted to Wilcox relates to a structure for connecting a piston and a piston rod adapted to permit a degree of universal movement therebetween to provide a valve action controlling the passage of fluid through the piston, e.g. for a damping dashpot for a sensitive electromagnetic assembly. The stated task is stated to be either or both of the following: (1) permit the piston rod a limited degree of universal movement without placing any strain on the piston itself; and (2) provide a structurally simple connection between the piston rod and piston which will provide for the transmission of movement from one to the other and which at the same time function as a directional valve. With reference to claim 1, the invention is a piston assembly comprising "a member oppressively connected to said piston [at a given end] . . . for angular movement relative thereto", the improvement of the assembly being "said piston assembly including an element having a chamber opening onto said given end of said piston, said member extending into said chamber and having a ball-like part ratably received therein with air-flow clearance between itself and said chamber." The intent of the patent is to allow the transfer of fluid between the fore and aft areas of the cylinder as separated by the piston which permits air-flow therebetween. The universal or angular movement of the member and piston is incidental to the accomplishment of air-flow through the piston, the described "improvement" . (As will be more apparent hereinafter in the discussion of the instant invention, the intent to allow the transfer of fluid is different from the present invention whose objective is to accomplish total fluid separation between piston and barrel areas of the syringe.

Finally, for the sake of full candor, Italian Patent No. 708,474 to Nogier et al. was also found. Applicant can review the patent drawings but is unable to read the text. Although it appears from FIG. 3 that the plunger 1 may be flexibly attached at neck 8 to the piston 7, it appears that the piston is made of flexible rubber rather than glass.

SUMMARY OF THE INVENTION

In accordance with the present invention, this task is solved in a simple an elegant manner by re-designing the plunger/barrel assembly in order to eliminate the inherent misalignment imparted by the human hand to the plunger and barrel assembly by the addition of a flexible movement to the leading end of the plunger. This novel flexible movement prevents lateral forces imparted to the rear end of the plunger from being transmitted into lateral forces applied to the leading end of the plunger, thereby causing the plunger to drag or stick within the syringe barrel.

Whereas the common glass plunger of the prior art is of unitary construction, in the preferred embodiment of this invention, the plunger will be of two-part construction in which the first part of the plunger is a glass tip ground to fit within the barrel in the usual manner; and the second part is a plunger handle member flexibly secured to the glass plunger tip, preferably to its distal or leading end, so that the second member is free to flex at the attachment point. This limits the forces applied to the plunger member to axial forces implied to the glass plunger tip component so that it becomes self-centering as it moves forward within the barrel, thereby eliminating the heretofore described limitations of sticking or freezing.

As shown in the illustrative drawings to be discussed hereinafter, the connection of the second component of the plunger to the first component is preferably made at the leading or distal end of the glass tip so that lateral forces applied to the plunger member are, in turn, converted to axial forces applied to the glass plunger tip.

However, Applicant has also successfully reduced to practice an alternate embodiment wherein the second component of the plunger is attached rearward within the trailing or proximal end of the glass tip.

BRIEF DESCRIPTION OF THE DRAWINGS

FIGS. 7a–c are views of another embodiment of a syringe plunger of this invention in which FIG. 7a is an exploded perspective view of its component parts; FIG. 7b is an exploded elevational view of the plunger; and FIG. 7c is an elevational view similar to FIG. 7b showing the assembly of the component parts.

DETAILED DESCRIPTION OF THE INVENTION

As was described previously in detail, matched ground glass syringes have the ability to provide a smooth, friction-free movement of the syringe plunger within the barrel, making them particularly efficacious in medical procedures such as the administration of epidural anesthesia by the "loss of resistance" technique. Yet, while they can function in the desired manner when the plunger is advanced axially within the barrel, there tends to be from time-to-time what is preferred to in the art as "sticking" or "freezing up" due to non-axial movement within the barrel, which non-axial movement will, at the least, cause the procedure to be suspended while the syringe is replaced by a new one; and, in the worst case, can put the patient at risk.

Stated simply, it is the task of the present invention to provide a ground glass syringe having all of the advantages of low friction in usage while at the same time obviating the occasional problem of sticking or freezing up inherent in the use of the prior art ground glass syringes.

For a complete understanding of the nature and objects of the present invention, reference is made to the following detailed disclosure taken in conjunction with the illustrative drawings.

Figure 1A:
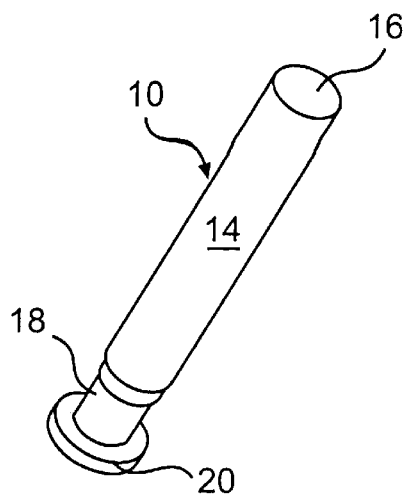
FIGS. 1(a–c) is a perspective view showing the plunger (FIG. 1a) and barrel (FIG. 1b) of a typical glass epidural syringe of the prior art first with the two components separate and then (FIG. 1c) with the plunger within the bore of the barrel.

FIG. 1(a) shows a conventional ground glass syringe of the prior art, the modification of which is the task of the present invention. As shown, the syringe consists of a plunger 10 and a barrel 12. Plunger 12 has a tubular body 14 terminating in a distal end 16 and tapering proximally with a neck portion 18 to a proximal generally flat, circular disc 20 at its proximal end adapted to accommodate the thumb of an anesthesiologist. The plunger has at least its tubular body portion 14 ground or chemically etched to provide a smooth, precise, low friction surface.

Figure 1B:
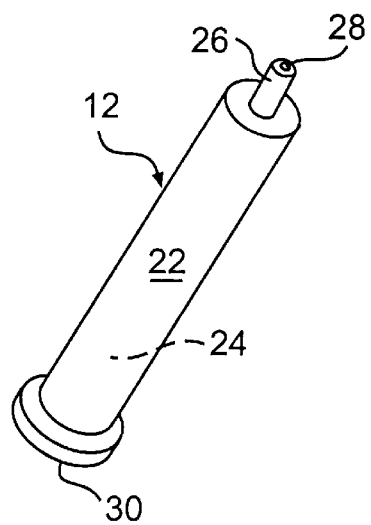

The barrel 12 shown in FIG. 1(b) has a tubular portion 22 having a distal end 26 having an opening 28 for dispensing the contents of the barrel when compressive pressure is exerted by the plunger seated within; and a proximal end 30 which is open to receive plunger 10. The inner surface of tubular body portion 22 of barrel 12 is also ground or chemically etched to provide a smooth, precise, low friction surface.

Figure 1C:
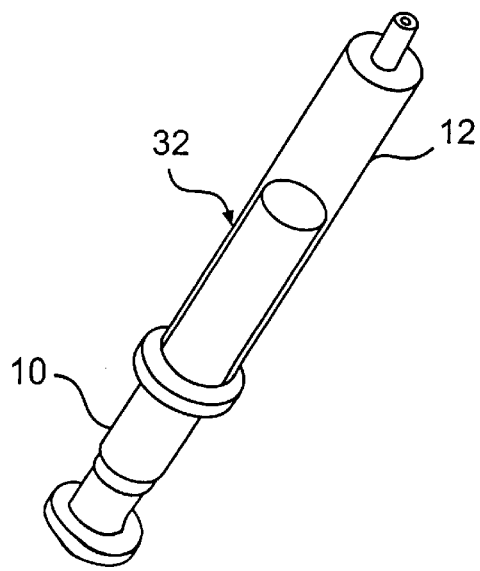

FIG. 1(c) depicts the composite structure with the barrel 12 with plunger 10 seated within defining the known syringe 32.

The matched ground or etched surfaces of the plunger and barrel provide a smooth, friction-free contact area which is air and liquid tight. The precision contact surface between the internal surface of the barrel and the external surface of the plunger provides an effortless movement between the respective surfaces. This seemingly friction-free movement is apparent whether the syringe is full of air, liquid or a combination thereof.

As the result of this elegant contact, the syringe plunger will transmit the subtle differences in plunger pressure so important to the skilled anesthesiologist when approaching the epidural space.

Figure 2:
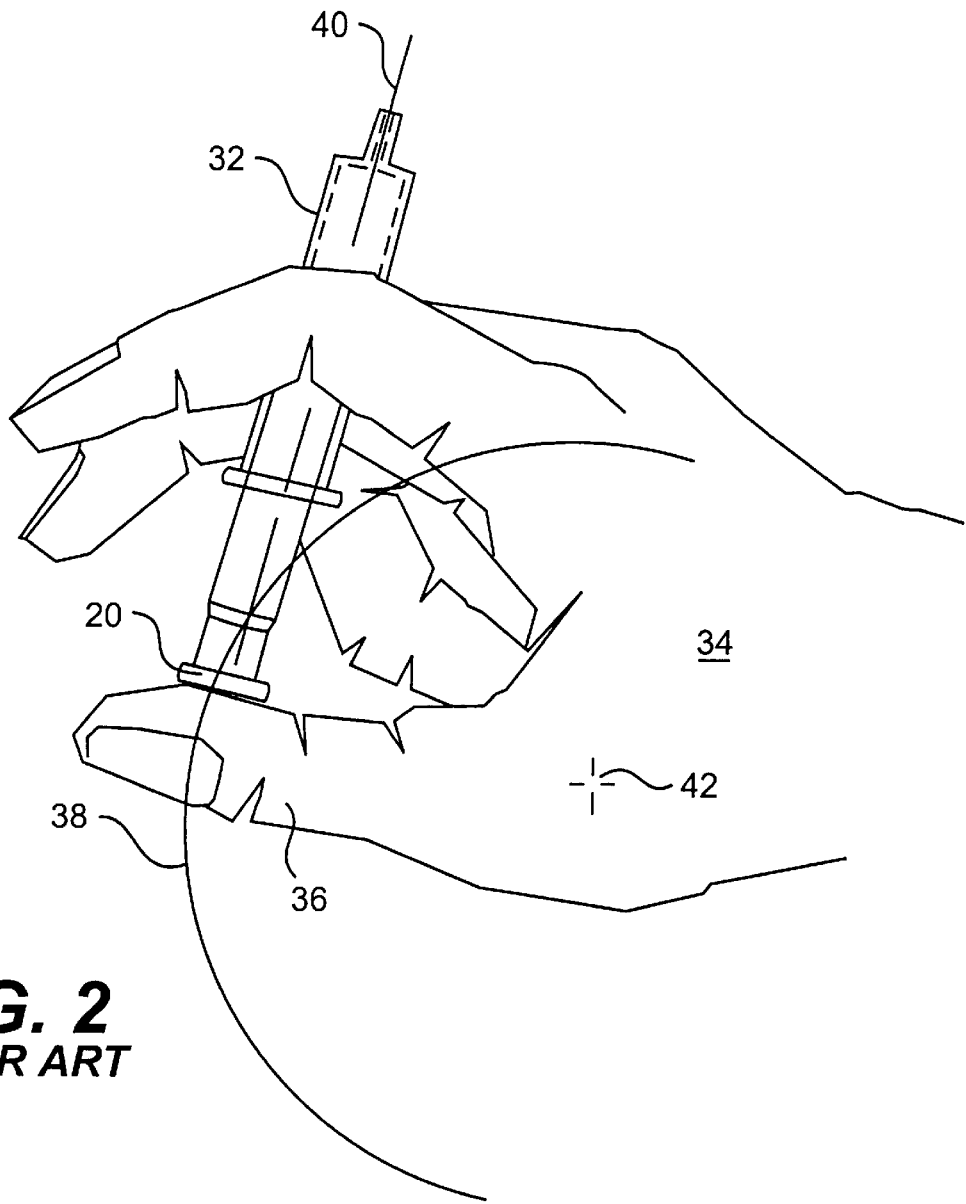
FIG. 2 is an elevational view of a practitioner's hand holding the syringe of FIG. 1 for precise manipulation of the syringe assembly and for administration of anesthesia to a patient.
Figure 3:
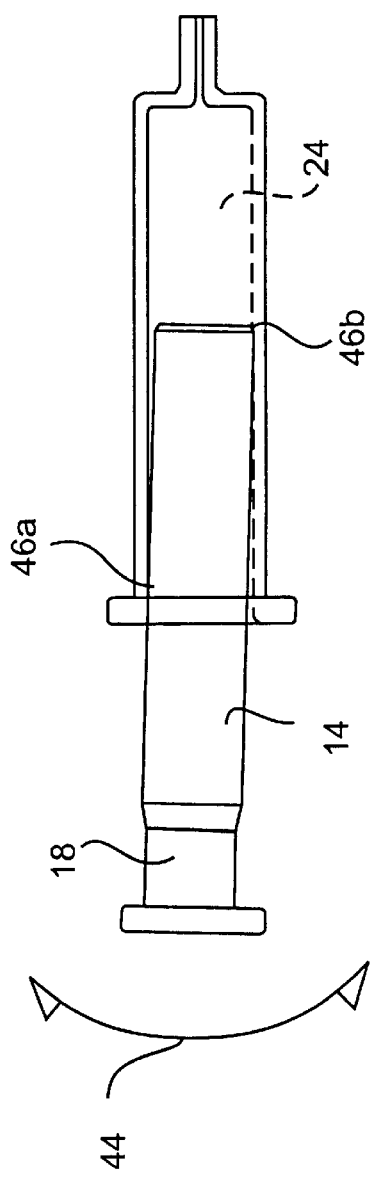
FIG. 3 is an elevational view showing the non-axial misalignment of the plunger as it advances within the barrel of the syringe of FIG. 1, causing the problem to which the present invention is directed.

FIGS. 2 and 3 together illustrate the cause of the problem in the use of a conventional glass syringe as shown in FIG. 1 to which the present invention is directed.

With reference first to FIG. 2, a hand 34 of an anesthesiologist is shown holding a syringe 32 as illustrated in FIG. 1. In known manner, the anesthesiologist applies pressure to the plunger in a constant or intermittent manner with the thumb 36 pressing against disc 20. When the thumb applies pressure to the proximal end of the plunger as illustrated, the thumb describes an arc of motion 38. As the plunger then moves forward within the barrel 12 along axis 40, the force applied by the thumb to plunger becomes more tangential due to the arc-like motion of thumb 36 as it pivots about thumb joint 42. This misalignment of motion between arc 38 and axis 40 in turn results in the application of lateral forces directed to the plunger 10 and barrel 12 contact surfaces, thereby causing the plunger to stick or freeze up inside the barrel.

With reference next to FIG. 3, the known plunger/barrel assembly is illustrated showing the plunger with lateral forces 44 applied to its proximal end 18. As can be seen, the result of these lateral forces is a first contact point 46a between the surface of plunger body 14 and the inner surface 24 of the barrel 12. A second contact point 46b is simultaneously created between the plunger and barrel surfaces. These contact points are the basis for and result in the sticking, dragging and freezing up complaints by clinicians inherent with the use of glass syringes of the low friction ground surface type.

Having thus described in detail the state of the art relating to low friction ground glass syringes at the time the present invention was made and the problems which will occur from time to time in their use, attention is now invited to Applicant's solution to the stated task of obviating these problems.

Figure 4:
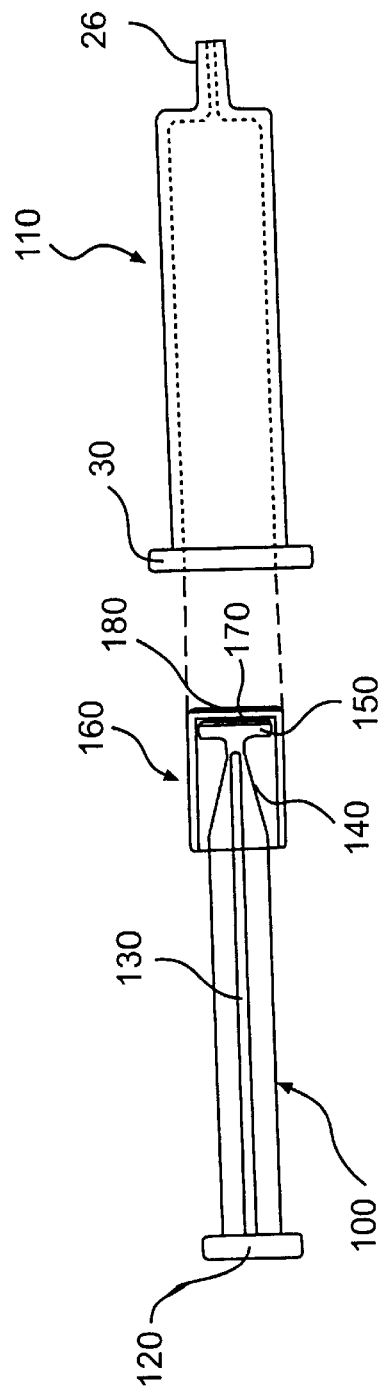
FIG. 4 is an exploded elevational view of a preferred syringe of the present invention showing the plunger separate from the barrel.

FIG. 4 illustrates a preferred embodiment of this invention having a novel self-aligning plunger member 100 mated with a per se known ground or etched glass barrel 110 such as barrel 12 shown in FIGS. 1–3. However, while conventional plunger 10 of the prior art is of a single member ground glass configuration, the plunger 100 embodying the present invention is shown to consist of two members, 130,160 secured together so as to provide a unitary plunger. These two members may be described as rearward or proximal plunger member 130 and a forward or distal plunger member 160. For purposes of discussion, member 130 may be described hereinafter in the description and the appended claims as the handle member 130 of the plunger. The handle member 120 need not be made of ground glass, but may instead be made of a suitable molded polymeric material, e.g. polyethylene, polypropylene, etc. It also may be of various configurations other than circular to fit within the bore of the barrel member. In the embodiment of FIG. 4, it is preferably made of a semi-rigid plastic material in which the rearward or proximal portion 130 consists of a finger pad of conventional design, tapering distally to terminate with a flexible end section 140 and a forward mounting section 150. At its proximal end, handle 130 terminates in a conventional flat disc of conventional design similar to disc 20 shown in FIGS. 1a and 2.

Figure 4A:
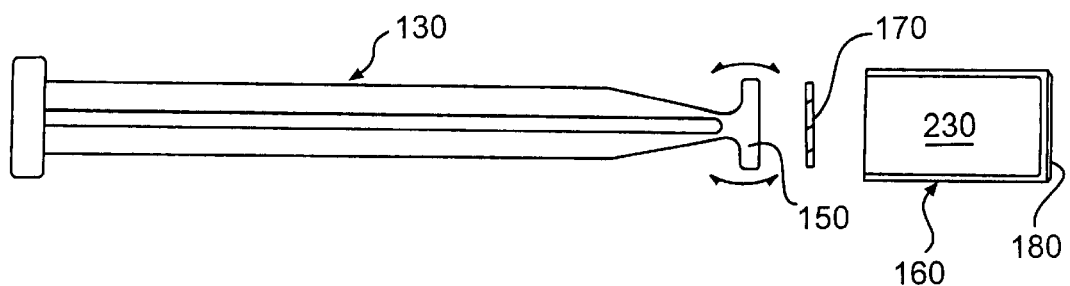
FIG. 4a is an exploded elevational view showing the individual components of the plunger of the syringe shown in FIG. 4.

The proximal member of the plunger need not be of conventional configuration so as to fit closely within the barrel bore, as is essential with the syringe plungers of the prior art simply because the distal member 160 of the self-aligning plunger of this invention in the embodiment of FIGS. 4, 4a consists of a ground or etched glass of known and current design. Distal member 160 is manufactured in the conventional manner so as to match with the glass syringe barrel 110 of conventional design, ground or etched for a precision fit adapted for ease of advancement axially towards the tip of barrel 26.

The rearward plunger member 130 of the self-aligning syringe piston is attached within bore 230 by attaching means 170 to the distal end 180 of glass member 160. The attaching means may, for example, be a suitable adhesive, e.g., a per se known epoxy resin formulation, sufficient to bind the respective members sufficiently so as to maintain a permanent relationship preventing separation as the plunger is retracted within the barrel 110 during the process of syringe aspiration.

Figure 6:
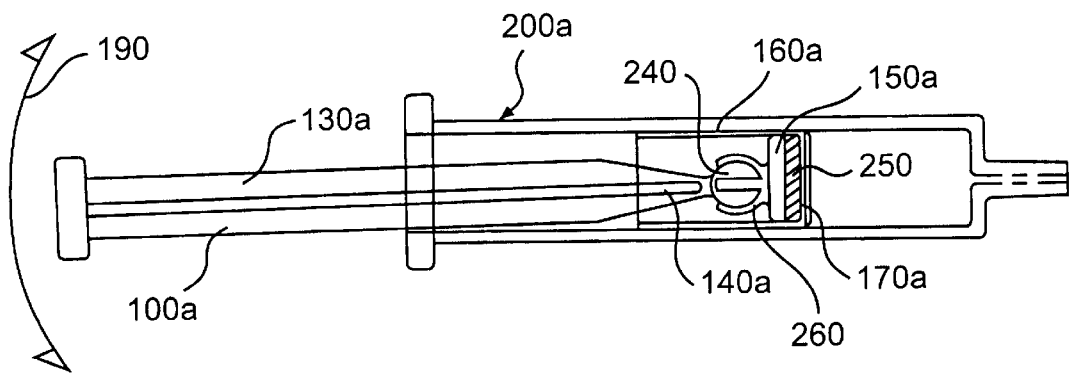
FIG. 6 is an exploded elevational view similar to FIG. 4 of an alternate embodiment of this invention.

The attachment between the rearward member 130 and the glass distal member 160 may also be advantageously achieved by mechanical means, an illustration of which is shown in FIG. 6.

Figure 5:
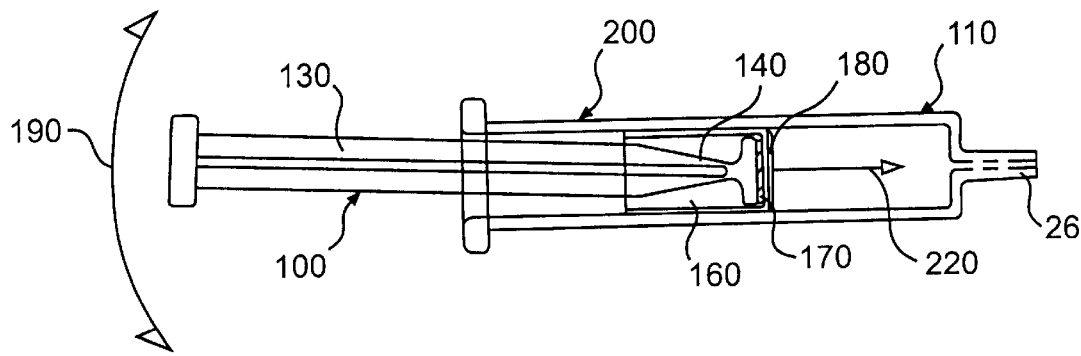
FIG. 5 is a similar view to FIG. 3 showing the misalignment of the proximal portion of the plunger 4 of this invention seated within the barrel of the syringe.

However, before discussing FIG. 6, attention is first invited to FIG. 5.

The novel plunger of the syringes of this invention have been previously described as "self-aligning". This feature of the invention is illustrated in FIG. 5 wherein, analogous to FIG. 3, when lateral forces 190 are applied to plunger 100 of a syringe 200 of this invention, whereas the rearward member 130 of plunger 100 may become misaligned, analogous to the misalignment of plunger 14 of the prior art syringe as illustrated in FIG. 3, self-alignment along the axis 220 of the novel plunger of this invention is provided by flexible member 140 of proximal member 130 fixedly secured to the glass distal member 160 of the plunger, thereby permitting the plunger to advance axially within barrel 110 of syringe 200 in the desired effortless, smooth, precise manner, thus obviating the contact points shown in FIG. 3 which in turn cause the sticking or freezing up problem which is the task of this invention.

Reference is now made to FIG. 6 illustrating an embodiment of this invention wherein mechanical means are provided for attaching the proximal and distal members of the plunger to provide flexible means for obtaining self-alignment in accordance with this invention.

As seen in FIG. 6, the mechanical attachment is achieved in an elegant but simple manner by a per se known ball and receiver assembly in which ball 240 secured by mounting means 150a to flexible member 140a of the proximal member 130a is movably retained within socket 260 fastened by mounting means 250 to the distal end 170a of glass member 160a of the plunger 100a. Since ball 240 is free to rotate within socket 260 when lateral forces 190 are applied, self-alignment is achieved in the same manner described with reference to FIG. 5, thereby permitting the glass distal end of the plunger to advance axially within the barrel without any sticking or freezing up. The mounting means 250 per se does not comprise any part of this invention and its selection will be a mere matter of choice within the expected judgment of the personnel charged with the commercial manufacture of the syringe of this invention. Useful means for attachment of the ball to the proximal member may, for example, include adhesion techniques, injection molding of the proximal member as a single component, etc. As will be appreciated, irrespective of the manner in securing the ball to the proximal member, the ball and socket assembly may be made before the socket is secured to the distal member of the plunger, e.g., by suitable mounting means 250.

Regardless of the manner of assembly, it will be readily understood that, as previously discussed, if the proximal member tends to become misaligned, the movement of the ball within the socket will permit the glass distal member to continue to advance axially within the barrel of the syringe.

Figure 7A:
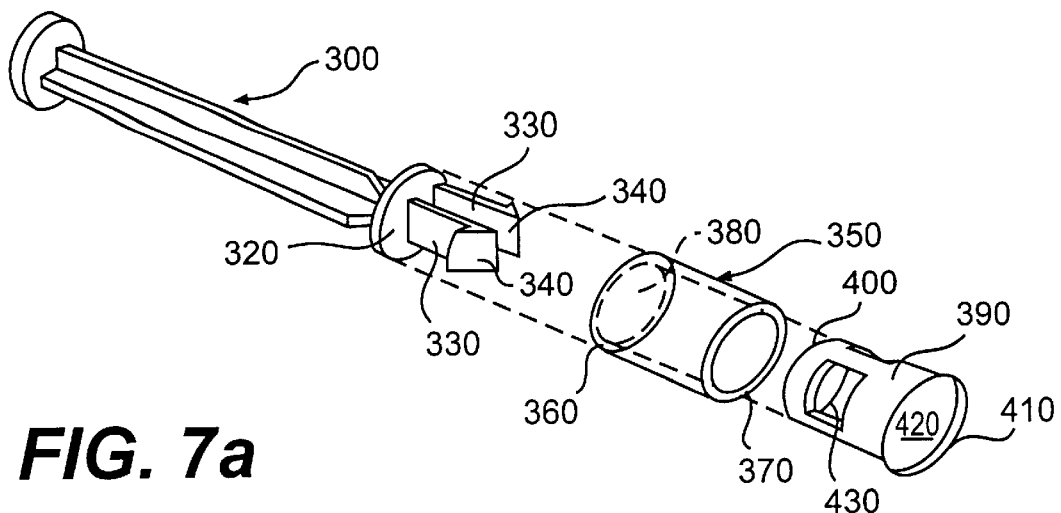

FIG. 7 illustrates another embodiment of this invention wherein mechanical attachment of the leading and trailing members of the plunger provide the flexing for the self-alignment feature of the invention to obviate axial misalignment caused by the exertion of lateral forces on the trailing end or handle of the plunger.

As shown, the plunger 300 has essentially three component parts, namely a handle or proximal plunger member 305, a distal glass plunger member 350; and a locking member 390 insertable within the glass member 350 (as will be discussed hereinafter) to secure plunger member 305 within glass member 350.

The proximal member 305, which may, for example, be made of a semirigid plastic, has a flexible leading end 310 secured to the proximal or rear surface of disc 320.

A pair of flexible arms 330 having latching edges 340 are secured to the distal or front surface of disc 320.

Glass member 350, as in the previously discussed embodiments, is generally cylindrical in shape and of an external diameter such that it will fit closely within the syringe barrel (not shown). The glass member 350 has trailing and leading ends 360,370, respectively, which are open to define a chamber 380 the external surface of which, as in the previously discussed embodiments, is ground or chemically etched so as to move smoothly in axial alignment with the conventional precision ground or etched glass barrel of the syringe.

Figure 7B:
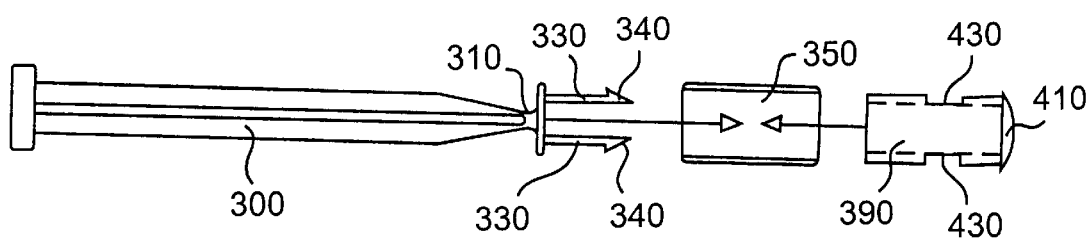
Figure 7C:
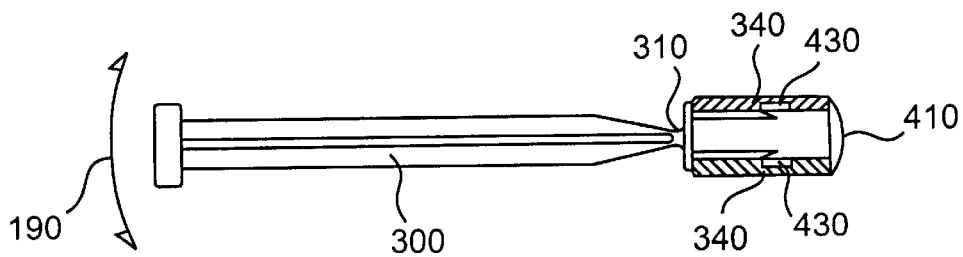

Locking member 390 has an open trailing end 400 and a closed leading end 410 defining chamber 420. With reference to FIGS. 7b and 7c, the three components are assembled by first sliding locking member 390 within the chamber 380 of glass member 350 and then sliding the proximal handle member 305 within the chamber 420 of locking member 390 until disc 320 abuts the trailing end 360 of the glass member 350 and the latching edges 340 slide within notches 430 in the wall of the locking member 390, thereby securing the component parts together as seen in FIG. 7c.

Figure 8:
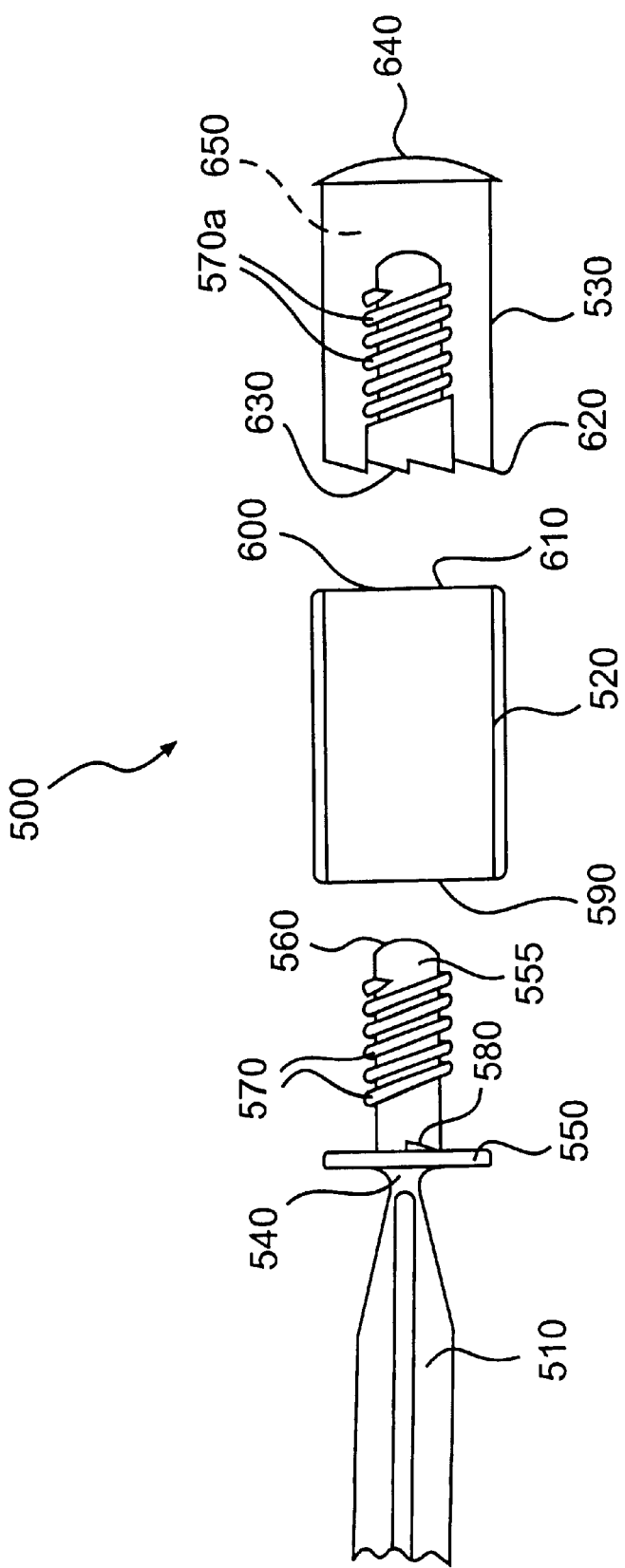
FIG. 8 is an exploded elevational view of yet another embodiment of the invention in which the trailing end of the plunger (not shown) is fractured or broken away.

FIG. 8 illustrates still another embodiment of this invention wherein mechanical means are provided to secure together the component parts of the novel syringe of this invention.

The syringe 500 of FIG. 8 also has three essential parts, namely a handle member 510, a glass member 520 and a locking member 530.

Since the trailing end of handle member 510 is similar to the trailing ends of the previous handle members of this invention and is not essential to an understanding of this embodiment the invention, handle member 510 is shown with the trailing end of the handle broken off. As with the embodiment of FIG. 7, handle member 510 terminates at its leading end with a flexible tip 540 secured to disc 550. An elongated tubular member 555 having male threads 570 has a free leading end 560 and is secured at its trailing end to the front surface of disc 550. For reasons to be apparent hereinafter, a pair of opposed ratchet teeth 580 are also provided on the front surface of disc 550.

Glass member 520, similar to glass member 350 of FIG. 7, has open proximal and distal ends 590,600, respectively, defining a cylindrical chamber 610, the external surface of which is precision ground or etched to provide a smooth surface which will move axially within a conventional precision ground or etched glass barrel.

The locking member 620 has an open trailing end 630 for receiving tubular member 555 within its chamber 650 and a closed leading end 640. As seen, trailing end 630 is provided with ratchet teeth 630. The locking member also has a female thread 570a adapted to mate with thread 570 to secure the two members together.

The manner of assembly is similar to that of the embodiment of FIG. 7 in that members 510 and 620 close within glass member 520 from opposite ends to provide the novel plunger.

Specifically, locking member 620 is inserted through open end 600 of the glass member until closed end 640 of the locking member is fully inserted into chamber 610 with its end 640 abutting end 600 of the glass member. Tubular member 555 is then threaded within open end 630 of the locking member, the male threads 570 of the tubular member 570 mating with the female threads 570a, until disc 555 abuts open end 590 of the glass member. When so inserted, ratchet teeth 580 on disc 555 mate with ratchet teeth 630 on the open end 620 to prevent the members 510 and 640 from accidental movement within the glass member, much less from being separable.

As will be readily understood from the foregoing description and the illustrative drawings, the self-aligning syringe plunger of this invention achieves the stated task of the invention by its ability to allow the glass distal member of the plunger to align itself axially within the glass barrel and to remain axially aligned irrespective of the lateral forces exerted against the rearward portion of the plunger so that these lateral forces applied cannot cause the limitations of the conventional glass syringe known as sticking or freezing up.

The self-aligning provided by the invention is accomplished by means of the flexibility afforded between the rearward portion of the syringe plunger and the ground or etched glass leading end of the syringe plunger.

In the preceding description of the invention, the connection of the flexible means at the distal end of the rearward member to the glass component is shown to be made at the inner or rear surface of the distal end of the glass component. This is preferred in order to assure that the lateral forces imparted to the plunger do not result in any misalignment of the glass component, the only element critical to this invention which must maintain axial alignment during advancement of the plunger within the syringe barrel.

In addition to solving the stated task of this invention, the present invention also provides certain other advantages over the glass plunger/barrel syringes of the prior art.

One of these advantages is that the anesthesiologists need not focus any attention on obviating misalignment of the plunger. The self-aligning feature of the invention takes care of that concern. Instead, they can devote all of their attention to the correct placement of the epidural needle within the epidural space.

Another advantage is that minor discrepancies in the manufacturing process of the glass components are minimized in use as would be the case with the prior art glass syringes.

Yet another feature of this invention is that the construction of the plunger assembly can be separated into the precision of the construction of the glass component as separate from the relative imprecision of the construction of the trailing plunger member. This division will by no means denigrate the function of either component.

Still another advantage is the cost saving in materials and manufacture of the trailing plunger member, leaving precision grinding only to the smaller leading plunger component.

A still further advantage inherent in solving the task of the invention, but worth mention, is the benefit to both the patient and the entire operating room staff that the procedure is not interrupted or delayed with the needle left unattended in the interspinous ligaments while awaiting location of another syringe.

The present invention also provides certain improvements over the low friction syringes described and claimed in Applicant's aforementioned U.S. Pat. No. 5,397,313 for LOW FRICTION SYRINGE which describes improvements in plastic syringes using elastomeric gaskets of low interference between the gasket and plastic syringe barrel.

The intent of this patent is to achieve the effortless movement of the elastomeric syringe plunger within the plastic barrel while eliminating the limitations inherent in the glass syringe by replacement of plastic for the glass.

While the '313 patent accomplishes this task, the accomplishment is not without creating other lesser disadvantages, namely, the increase in force that is required to move the plunger within the barrel.

As distinguished therefrom, the forces required to move a glass plunger within a matched glass barrel are admittedly of the lowest degree if not realistically nonexistent. The novel plunger of the present invention is equivalent to the matched glass plunger in the force required for movement within the glass barrel. For this reason, the lack of resistance in matched ground or etched glass syringes is the syringe of choice by medical practitioners barring any manifestations of sticking or freezing up, an inherent tendency completely obviated by the self-aligning plungers of the present invention.

While the present invention has been described in detail so as to enable those skilled in the art to practice same, it is intended that the foregoing description taken in conjunction with the accompanying drawings be taken as being illustrative and not in a limiting sense.

What is claimed is:

1. A syringe plunger adapted for use in a glass syringe barrel for administering epidural anesthesia, the plunger having a first or forward member and a second or rearward member;

the first member comprising a hollow glass tip defining a chamber having a closed leading end and an open trailing end, the glass tip being characterized as adapted to provide a very close tolerance fit within a glass syringe barrel and as exhibiting substantially no frictional interference as the leading end of the glass tip is advanced within the glass barrel of the syringe;

the second member having leading and trailing ends; and means for flexibly securing the leading end of the second member within the chamber of the first member so that the rearward first member is free to flex at the point of attachment in response to lateral forces applied to the second member as it is advanced within the glass barrel during use, the plunger thereby being characterized as being self-aligning as the plunger is advanced within the syringe barrel, thereby preventing the lateral forces so applied to the plunger during use from moving the glass tip of the plunger out of axial alignment with the axis of the barrel, thereby to cause binding or dragging of the plunger within the barrel.

2. A syringe plunger as defined in claim 1 wherein at least the leading end of the second member secured to the first member is flexible.

3. A syringe plunger as defined in claim 2 wherein the means of securing the second member to the first member comprises an adhesive.

4. A syringe plunger as defined in claim 1 wherein the second member is flexibly secured within the chamber to the leading end of the first member.

5. A syringe plunger as defined in claim 1 wherein the means for flexibly securing the second member to the first member is mechanical.

6. A syringe plunger as defined in claim 5 wherein the mechanical means for flexibly securing the first and second members comprises a ball secured to one of the members mating with a socket secured to the other member, the ball being movable within the socket responsive to the lateral forces.

7. A syringe plunger as defined in claim 1 wherein the outer surface of the glass tip is precision ground or chemically etched to impart a very fine texture to mate with the interior surface of the glass barrel which has a similar texture.

8. A syringe comprising, in combination:

a glass syringe barrel having a circumferential inner surface defining a chamber having an opening at its trailing end for insertion of a plunger to administer a fluid to a patient and a small opening at its leading end through which the fluid contents of the barrel is ejected, the inner surface of the barrel being precision ground or chemically etched to impart a very fine texture to the surface; and a syringe plunger as defined in claim 1.

9. A syringe as defined in claim 8 wherein the outer surface of the glass tip of the plunger is also precision ground or chemically etched to provide a surface mating with the interior surface of the barrel, the exterior surface of the glass tip being seated within the barrel in close proximity with the inner surface of the barrel such that, although they do not touch when the plunger advances axially within the barrel chamber, the close proximity entraps air or liquid molecules between their respective surfaces sufficient to create an air- and liquid-tight interface, the close fit providing an effortless seal between the plunger and barrel.

10. A syringe adapted for administering epidural anesthesia comprising, in combination:

a glass barrel having a circumferential inner surface defining a chamber having an opening at its trailing end for insertion of a plunger and a small opening at its leading end through which fluid contents within the barrel is ejected responsive to advancement of the plunger towards the leading end of the barrel;

a plunger removably insertable within the barrel, the plunger having a first or forward member and a second or rearward member, the first member comprising a hollow glass tube the circumference of which defines a chamber having a closed leading end and an open trailing end, the glass tube having an outer circumference providing a very close tolerance fit when the first member is seated within the glass barrel;

the second member having leading and trailing ends and being removably insertable within the barrel; and means for flexibly securing the leading end of the second member within the chamber of the first member in axial alignment with the barrel of the syringe, the second member thereby being free to flex at the point of attachment in response to lateral forces applied to the second member as it advances within the glass barrel during use without the lateral forces causing axial mis-alignment, the plunger thereby being characterized as being self-aligning.

11. A syringe as defined in claim 10 wherein the circumferential outer surface of the tubular first member and the circumferential inner surface of the barrel are each precision ground or chemically etched to provide mating surfaces which are characterized as possessing a smooth, fine texture.

12. A syringe as defined in claim 11 wherein the closeness of the tubular first member of the plunger to the inner surface of the barrel when the first member is seated within the barrel is such that, although the surfaces do not touch when the plunger advances within the barrel chamber, the close proximity entraps air or liquid molecules between the respective surfaces sufficient to create an air- and liquid-tight interface providing an effortless seal between the plunger and the barrel.

13. A syringe as defined in claim 1 wherein at least the leading end of the second member secured to the first member is flexible.

14. A syringe as defined in claim 13 wherein the means for securing the second member to the first member comprises an epoxy adhesive formulation.

15. A syringe as defined in claim 10 wherein the second member is secured within the chamber to the leading end of the first member.

16. A syringe as defined in claim 10 wherein the means for flexibly securing the second member to the first member is mechanical.

17. A syringe as defined in claim 16 wherein the mechanical means comprises a ball secured to one of the members and mating with a socket secured to the other member in a ball and socket arrangement.

18. In a procedure for locating a patient's epidural space preparatory to administering epidural anesthesia wherein a syringe is filled with air, liquid or a combination of both, attached to a needle and advanced through delicate tissues of the patient's spineous ligaments to the epidural space, the improvement wherein the syringe is a syringe as defined in claim 10.

* * * * *